US00PP17026P2

(12) United States Plant Patent
Meszaros

(10) Patent No.: US PP17,026 P2
(45) Date of Patent: Aug. 22, 2006

(54) ***PETUNIA* PLANT NAMED 'PETZEBRINA'**

(50) Latin Name: *Petunia×hybrida*
Varietal Denomination: Petzebrina

(75) Inventor: Debra Meszaros, Riverhead, NY (US)

(73) Assignee: Advanced Plant Technologies LLC, Riverhead, NY (US)

( * ) Notice: Subject to any disclaimer, the term of this patent is extended or adjusted under 35 U.S.C. 154(b) by 19 days.

(21) Appl. No.: 11/128,987

(22) Filed: May 13, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Petunia* plant named 'Petzebrina', characterized by its compact, mounding and outwardly spreading plant habit; freely branching growth habit; green and greenish white variegated foliage; and numerous dark pink-colored flowers with red purple-colored venation.

2 Drawing Sheets

Botanical designation: *Petunia×hybrida.*
Cultivar denomination: 'Petzebrina'.

BACKGROUND OF THE INVENTION

The present Invention relates to a new and distinct cultivar of *Petunia* plant, botanically known as *Petunia×hybrida,* and hereinafter referred to by the cultivar name Petzebrina.

The new *Petunia* is a naturally-occurring branch mutation of a proprietary *Petunia×hybrida* selection identified as PAF0101, not patented. The new *Petunia* was discovered and selected by the Inventor as a single branch from a flowering plant of the parent selection in a controlled environment in Riverhead, N.Y. in November, 2001.

Asexual reproduction of the new cultivar by vegetative cuttings in Riverhead, N.Y. since November, 2001, has shown that the unique features of this new *Petunia* are stable and reproduced true to type in successive generations.

SUMMARY OF THE INVENTION

Plants of the cultivar Petzebrina have not been observed under all possible environmental conditions. The phenotype may vary somewhat with variations in environment such as temperature and light intensity without, however, any variance in genotype.

The following traits have been repeatedly observed and are determined to be the unique characteristics of 'Petzebrina'. These characteristics in combination distinguish 'Petzebrina' as a new and distinct cultivar:

1. Compact, mounding and outwardly spreading plant habit.
2. Freely branching growth habit.
3. Green and greenish white variegated foliage.
4. Numerous dark pink-colored flowers with red purple-colored venation.

Plants of the new *Petunia* differ primarily from plants of the parent selection in leaf coloration as plants of the parent selection have solid green-colored leaves.

Plants of the new *Petunia* can be compared to plants of the cultivar Royal Frost, disclosed in U.S. Plant Pat. No. 11,516. In side-by-side comparisons conducted in Riverhead, N.Y., plants of the new *Petunia* differed primarily from plants of the cultivar Royal Frost in the following characteristics:

1. Plants of the new *Petunia* were more upright than plants of the cultivar Royal Frost.
2. Plants of the new *Petunia* were broader than plants of the cultivar Royal Frost.
3. Plants of the new *Petunia* and the cultivar Royal Frost differed in leaf and flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph on the first sheet comprises a side perspective view of a typical flowering plant of 'Petzebrina' grown in a container.

The photograph on the second sheet comprises a close-up view of typical leaves and flowers of 'Petzebrina'.

DETAILED BOTANICAL DESCRIPTION

The aforementioned photographs and following observations and measurements describe plants grown in Riverhead, N.Y., under commercial practice during the spring and summer in a polyethylene-covered greenhouse with day temperatures averaging 22° C., night temperatures averaging 17° C., and light levels ranging from 9,000 to 12,000 lux. Plants were grown for about 16 weeks in 25-cm containers. In the following description, color references are made to The Royal Horticultural Society Colour Chart, 1995 Edition, except where general terms of ordinary dictionary significance are used.

Botanical classification: *Petunia×hybrida* cultivar Petzebrina.

Parentage: Naturally-occurring branch mutation of a proprietary *Petunia×hybrida* selection identified as PAF0101, not patented.

Propagation:

*Type cutting.*—Vegetative cuttings.

*Time to initiate roots, summer.*—About 15 days.

*Time to initiate roots, winter.*—About 20 days.

*Time to produce a rooted young plant, summer.*—About three weeks.

*Time to produce a rooted young plant, winter.*—About four weeks.

*Root description.*—Fine, fibrous; white in color.

*Rooting habit.*—Freely branching, dense.

Plant description:

*Form.*—Annual flowering plant; indeterminate; initially upright, then mounding and outwardly spreading; compact. Moderately vigorous growth habit. Freely basal branching habit lateral branches potentially developing at every node.

*Usage.*—Appropriate for hanging baskets, window boxes, patio containers and landscape applications.

*Plant height.*—About 20 to 25 cm.

*Plant diameter.*—About 50 to 60 cm.

*Lateral branches.*—Length: About 28 cm. Diameter: About 2 mm. Internode length: About 1 cm. Texture: Pubescent. Color: 139D.

*Foliage description.*—Arrangement, before flowering: Alternate, simple. Arrangement, when flowering: Opposite, simple. Length: About 2.5 to 3.5 cm. Width: About 1.5 to 2.5 cm. Shape: Ovate. Apex: Acute. Base: Obtuse. Margin: Entire. Texture, upper and lower surfaces: Viscid; pubescent. Venation pattern: Pinnate, arcuate. Color: Developing foliage, upper surface: Center, 141C; towards the margins, 150C. Developing foliage, lower surface: Center, 139C; towards the margins, 150C. Fully expanded foliage, upper surface: Center, 141B; towards the margin, 157D. Fully expanded foliage, lower surface: Center, 141C; towards the margin, 157D. Venation, upper and lower surfaces: Similar to lamina. Petiole length: About 1 cm. Petiole diameter: About 3 mm. Petiole texture, upper and lower surfaces: Pubescent. Petiole color, upper and lower surfaces: 139C.

Flower description:

*Flower type and habit.*—Salverform flowers; flowers face upward or outward; single, axillary. Freely flowering, typically about six open flowers and flower buds per lateral branch.

*Natural flowering season.*—Long day responsive; plants flower from April until frost in New York; flowering continuous during the flowering period. Plants start flowering about eight weeks after planting.

*Flower longevity on the plant.*—About one week; flowers not persistent.

*Fragrance.*—None detected.

*Flower size.*—Diameter: About 6 cm. Depth: About 3.5 cm. Tube length: About 2.5 cm. Throat diameter, distal end: About 7.5 mm. Tube diameter, proximal end: About 2.5 mm.

*Flower buds.*—Length: About 3 cm. Diameter: About 5 mm. Shape: Elongated oblong with ruffled apices. Color: 50B to 58A.

*Corolla.*—Arrangement/appearance: Single whorl of five petals, fused into flared trumpet with distinct clefts between petal lobes. Petal lobe length: About 3 cm. Petal lobe width: About 3 cm. Petal shape: Roughly fan-shaped. Petal apex: Acute. Petal margin: Entire. Petal texture, upper surface: Smooth, satiny. Petal texture, lower surface: Pubescent. Color: Petal, when opening, upper surface: 66B. Petal, when opening, lower surface: 67A. Petal, fully opened, upper surface: 55A. Petal, fully opened, lower surface: 55B. Flower throat (inside): 58A. Flower tube (outside): 54B. Venation, upper petal surface: 57B. Venation, lower petal surface: 55B. Venation, throat: 58A. Venation, tube: Close to 55B.

*Sepals.*—Arrangement/appearance: Single whorl of five sepals fused at base, star-shaped. Length: About 2 cm. Width: About 6 mm. Shape: Linear. Apex: Acute. Margin: Entire. Texture, upper and lower surfaces: Pubescent. Color, upper and lower surfaces: 138B.

*Peduncles.*—Length: About 1 cm. Width: About 2 mm. Angle: About 45° to the stem. Strength: Strong. Texture: Pubescent. Color: 138B.

*Reproductive organs.*—Stamens: Quantity/arrangement: Five per flower; stamens adnate to corolla tube. Anther shape: Oval. Anther length: About 7 mm. Anther color: 155A. Pollen amount: Moderate. Pollen color: 155A. Pistils: Quantity: One per flower. Pistil length: About 2 cm. Stigma shape: Rounded. Stigma color: 150B. Style length: About 1.6 cm. Style color: 141C. Ovary color: 141C.

*Fruit/seed.*—Fruit and seed production has not been observed.

Disease/pest resistance: Plants of the new *Petunia* have not been noted to be resistant to pathogens and pests common to *Petunia*.

Temperature tolerance: Plants of the new *Petunia* have been observed to tolerate temperatures ranging from 2 to 32° C.

It is claimed:

1. A new and distinct cultivar of *Petunia* plant named 'Petzebrina', as illustrated and described.

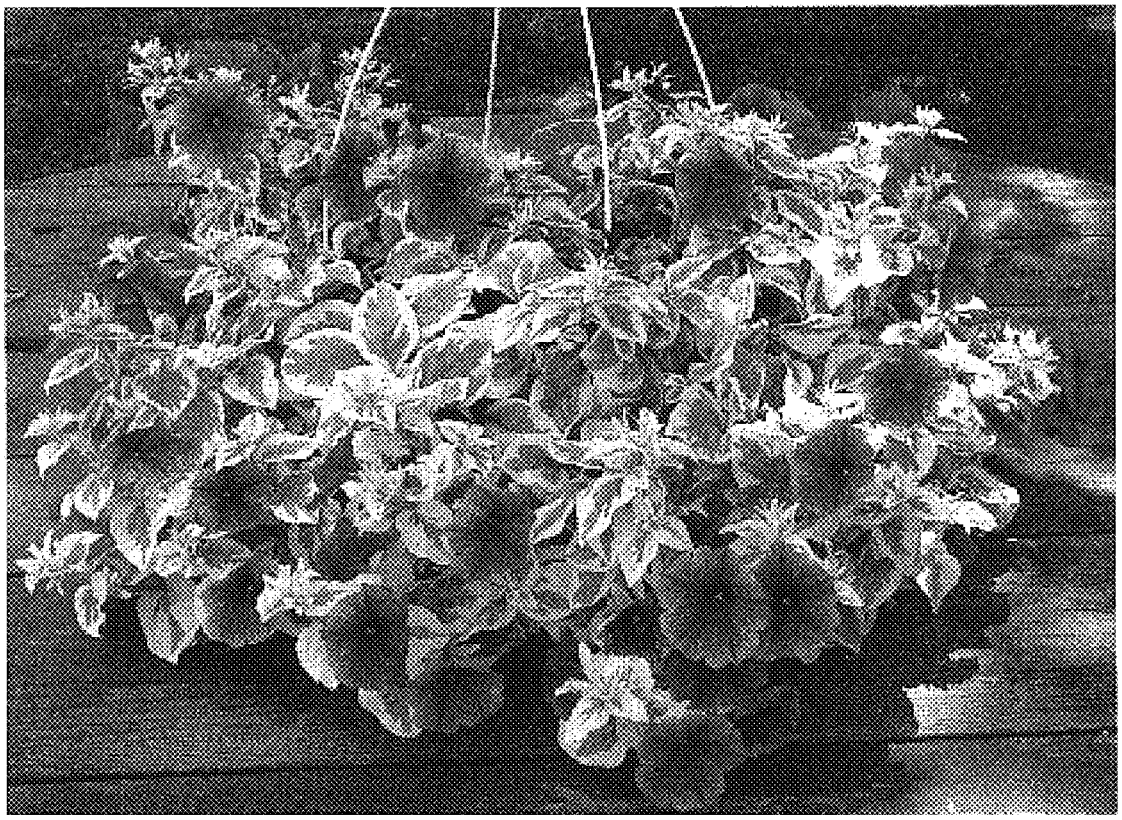

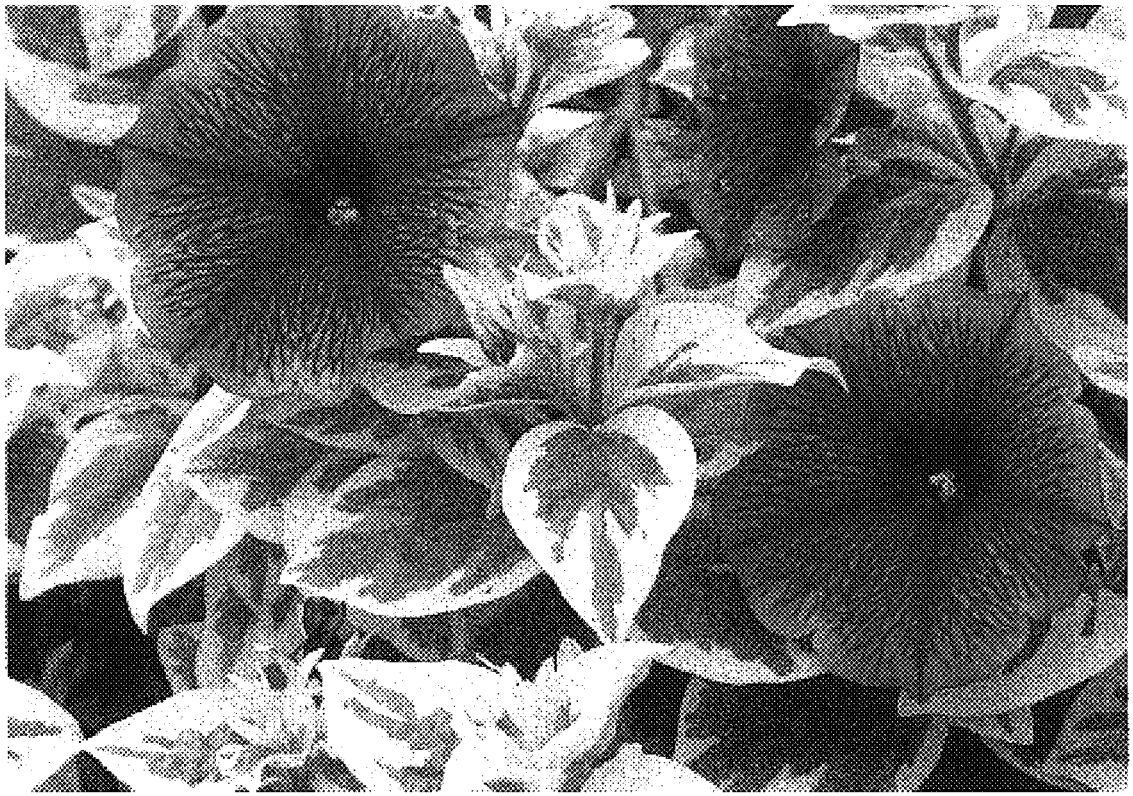

* * * * *